United States Patent
Iwase et al.

(10) Patent No.: US 9,025,844 B2
(45) Date of Patent: May 5, 2015

(54) IMAGE PROCESSING APPARATUS AND METHOD FOR CORRECTING DEFORMATION IN A TOMOGRAPHIC IMAGE

(75) Inventors: Yoshihiko Iwase, Yokohama (JP); Akihiro Katayama, Zama (JP); Daisuke Furukawa, Antibes (FR); Takeshi Kitamura, Port Washington, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 316 days.

(21) Appl. No.: 13/457,973

(22) Filed: Apr. 27, 2012

(65) Prior Publication Data
US 2012/0288175 A1 Nov. 15, 2012

(30) Foreign Application Priority Data

May 10, 2011 (JP) .................................. 2011-105391

(51) Int. Cl.
*G06K 9/00* (2006.01)
*G06T 7/00* (2006.01)
*A61B 3/10* (2006.01)

(52) U.S. Cl.
CPC ............... *G06T 7/0028* (2013.01); *A61B 3/102* (2013.01); *G06T 2207/10101* (2013.01); *G06T 2207/30041* (2013.01)

(58) Field of Classification Search
None
See application file for complete search history.

(56) References Cited

U.S. PATENT DOCUMENTS

| | | | |
|---|---|---|---|
| 5,530,494 A | 6/1996 | Ogawa et al. | |
| 5,557,321 A | 9/1996 | Kohayakawa et al. | |
| 6,158,864 A | 12/2000 | Masuda et al. | |
| 6,327,375 B1 | 12/2001 | Matsumoto et al. | |
| 2008/0284981 A1 | 11/2008 | Fercher | |
| 2010/0142780 A1* | 6/2010 | Yasuno et al. | 382/131 |
| 2011/0134392 A1 | 6/2011 | Iwase et al. | |
| 2011/0137157 A1 | 6/2011 | Imamura et al. | |
| 2011/0234785 A1 | 9/2011 | Wanda et al. | |
| 2011/0242484 A1 | 10/2011 | Furukawa et al. | |
| 2012/0057127 A1 | 3/2012 | Iwase et al. | |
| 2012/0063660 A1 | 3/2012 | Imamura et al. | |
| 2012/0133950 A1 | 5/2012 | Suehira et al. | |

FOREIGN PATENT DOCUMENTS

JP 2007-130403 A 5/2007

* cited by examiner

*Primary Examiner* — Atiba O Fitzpatrick
(74) *Attorney, Agent, or Firm* — Fitzpatrick, Cella, Harper & Scinto

(57) ABSTRACT

In a tomographic image photographing apparatus, a deformation of a volume image is corrected accurately even if an object to be inspected moves when the volume image is acquired. An image processing apparatus acquires a tomographic image of the object to be inspected from combined light beams of return light beams, which is obtained by irradiating the object to be inspected with a plurality of measuring light beams, and corresponding reference light beams. In the image processing apparatus, a photographing unit obtains a tomographic image of a fundus with the plurality of measuring light beams, and a detection unit detects a retina layer from the tomographic image. Based on the detected retina layer, a fundus shape is estimated. Based on the estimated fundus shape, a positional deviation between tomographic images is corrected.

19 Claims, 11 Drawing Sheets

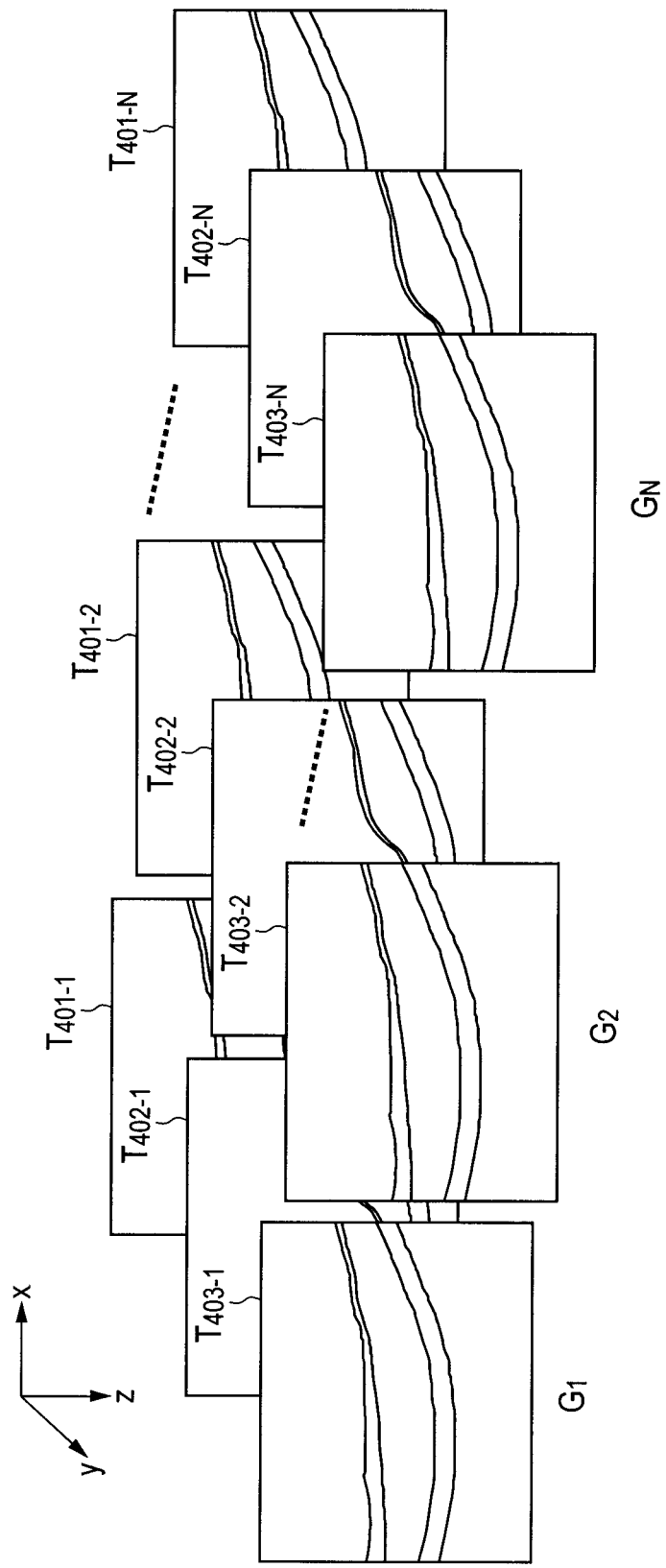

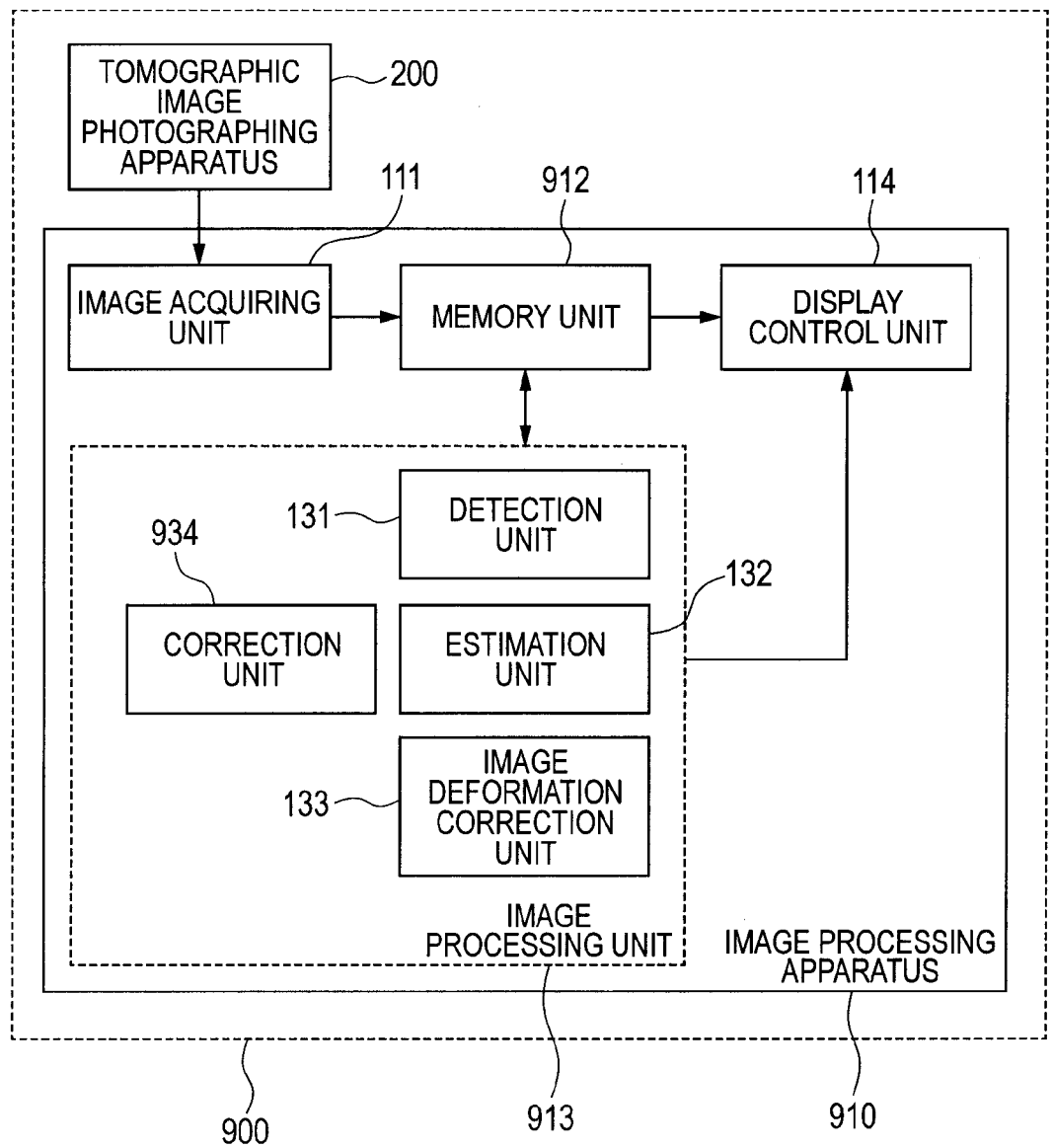

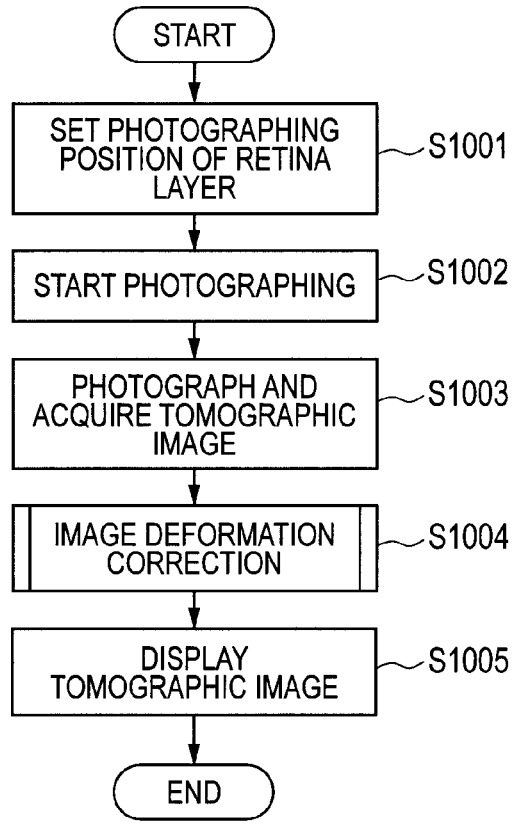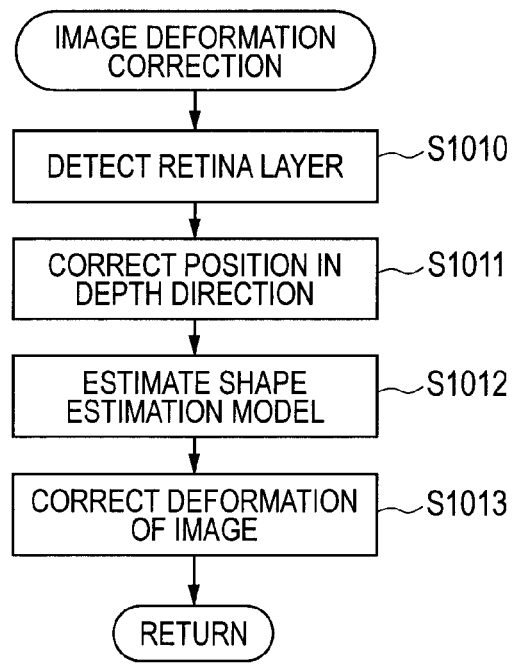

IMAGE PROCESSING APPARATUS AND METHOD FOR CORRECTING DEFORMATION IN A TOMOGRAPHIC IMAGE

BACKGROUND OF THE INVENTION

1. Field of the Invention

The present invention relates to an image processing apparatus and method, and more particularly, to an image processing apparatus and method for correcting a tomographic image used in ophthalmological diagnosis and treatment.

2. Description of the Related Art

A tomographic image photographing apparatus for eyes such as optical coherence tomography (OCT) is capable of three-dimensional observation of an internal state of a retina layer. This tomographic image photographing apparatus has been receiving attention in recent years because it is useful for accurate diagnosis of a disease.

The tomographic image photographing apparatus splits low coherent light into reference light and measuring light. The measuring light irradiates an object to be inspected, and return light from the object to be inspected and the reference light are caused to interfere with each other so that tomographic measurement of the object to be inspected can be performed. In other words, the measuring light scans the object to be inspected, to thereby obtain a two-dimensional tomographic image (hereinafter, referred to as a tomographic image) or a three-dimensional image (hereinafter, referred to as a volume image) as a set of plurality of tomographic images. However, if the object to be inspected is a living organism such as an eye, a deformation may occur in the volume image due to movement of the eye. Therefore, high-speed measurement with high sensitivity is required.

As one method for this, US 2008/0284981 discloses a method of simultaneously measuring a plurality of points of the object to be inspected. According to this disclosure, light from one light source is split into a plurality of light beams by using a slit. Then, the light beams are separated by a beam splitter into a plurality of measuring light beams and reference light. The measuring light beams irradiate the object to be inspected, and return light beams from the object to be inspected are combined with the reference light by the beam splitter. Then, the plurality of combined light beams enter a grating and are detected simultaneously by a two-dimensional sensor. In this way, according to US 2008/0284981, high speed measurement can be performed by simultaneously measuring with a plurality of measuring light beams.

In addition, Japanese Patent Application Laid-Open No. 2007-130403 discloses a configuration in which one measuring light beam is used, and an image for correction in the direction crossing a main scanning direction of the measuring light is formed when the volume image is generated. Then, the image for correction is used for correcting a deformation of the volume image.

In the configuration disclosed in U.S. Patent Publication No. 2008/0284981, high speed measurement can be performed by simultaneously measuring with a plurality of measuring light beams, but there is no disclosure concerning eye movement. If a volume image is generated, a deformation may occur in the volume image because a positional deviation occurs between neighboring tomographic images due to an influence of the eye movement.

In the configuration disclosed in Japanese Patent Application Laid-Open No. 2007-130403, a tomographic image for correction must be acquired for deformation correction of the volume image.

SUMMARY OF THE INVENTION

It is an object of the present invention to correct a deformation of a volume image accurately even if an object to be inspected moves when the volume image is acquired.

It is another object of the present invention to estimate a shape model from a plurality of tomographic images obtained by photographing spatially separated points at the same time in a volume image photographed with a plurality of measuring light beams without acquiring a tomographic image for correction, and to use the shape model for correcting a deformation of the volume image due to a positional deviation between the tomographic images.

In order to achieve the above-mentioned objects, an image processing apparatus according to an exemplary embodiment of the present invention has the following configuration.

An image processing apparatus according to an exemplary embodiment of the present invention includes; an image acquiring unit configured to acquire a three-dimensional image of a fundus of an eye to be inspected based on a plurality of combined light beams obtained by combining a plurality of return light beams from the eye to be inspected that is irradiated with a plurality of measuring light beams, and a plurality of reference light beams respectively corresponding to the plurality of return light beams, a detection unit configured to detect a retina layer from each of a plurality of tomographic images obtained by photographing the fundus at a predetermined timing among a plurality of tomographic images constituting the three-dimensional image, an estimation unit configured to estimate a fundus shape based on the detected retina layer, and a correction unit configured to correct a positional deviation between the plurality of tomographic images constituting the three-dimensional image based on the estimated fundus shape.

Further, an image processing method according to an exemplary embodiment of the present invention includes; acquiring a three-dimensional image of a fundus of an eye to be inspected based on a plurality of combined light beams obtained by combining a plurality of return light beams from the eye to be inspected that is irradiated with a plurality of measuring light beams, and a plurality of reference light beams respectively corresponding to the plurality of return light beams, detecting a retina layer from each of a plurality of tomographic images obtained by photographing the fundus at a predetermined timing among a plurality of tomographic images constituting the three-dimensional image, estimating a fundus shape based on the detected retina layer, and correcting a positional deviation between the plurality of tomographic images constituting the three-dimensional image based on the estimated fundus shape.

According to the present invention, it is possible to correct a deformation of the volume image without acquiring the image for correction.

Further features of the present invention will become apparent from the following description of exemplary embodiments with reference to the attached drawings.

BRIEF DESCRIPTION OF THE DRAWINGS

FIG. 7 is a diagram illustrating an example of parameter estimation.

FIG. 9 is a diagram illustrating a configuration of an image processing system according to another embodiment of the present invention.

FIGS. 10A and 10B are flowcharts illustrating process flows in the image processing system.

DESCRIPTION OF THE EMBODIMENTS

First Embodiment

Hereinafter, referring to the attached drawings, a first embodiment of the present invention is described. Note that, the image processing apparatus according to this embodiment estimates a shape model from a plurality of tomographic images obtained by photographing spatially separated points at the same time when photographing a volume image with a plurality of measuring light beams. Then, the shape model is used for alignment of neighboring tomographic images so that volume image deformation is corrected. Hereinafter, an image processing system including the image processing apparatus according to this embodiment is described in detail.

Figure 1:
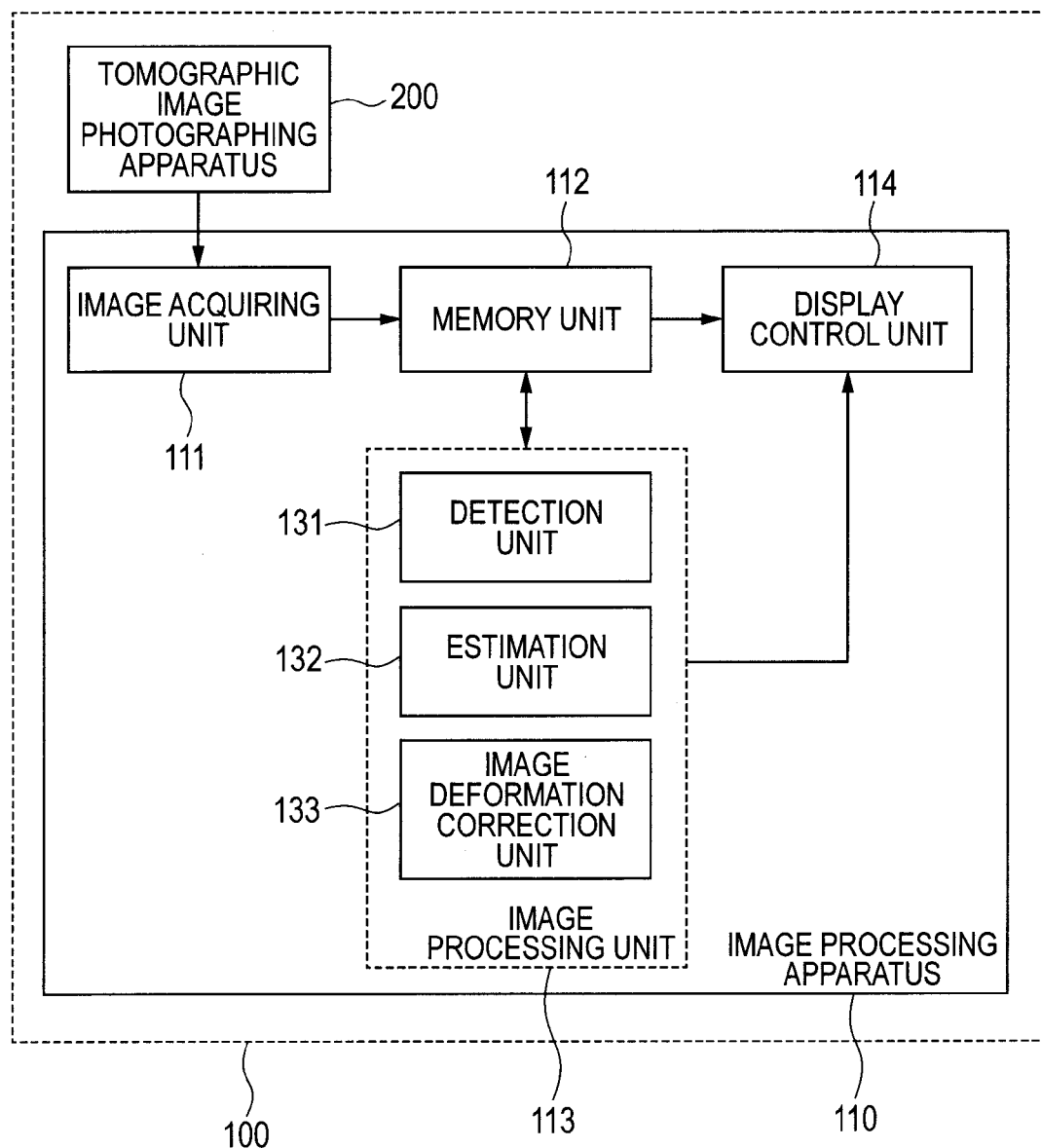
FIG. 1 is a diagram illustrating a configuration of an image processing system according to an embodiment of the present invention.

FIG. 1 is a diagram illustrating a configuration of an image processing system 100 including an image processing apparatus 110 according to this embodiment. As illustrated in FIG. 1, the image processing system 100 has a configuration in which the image processing apparatus 110 is connected to a tomographic image photographing apparatus 200 via an interface.

Figure 2A:
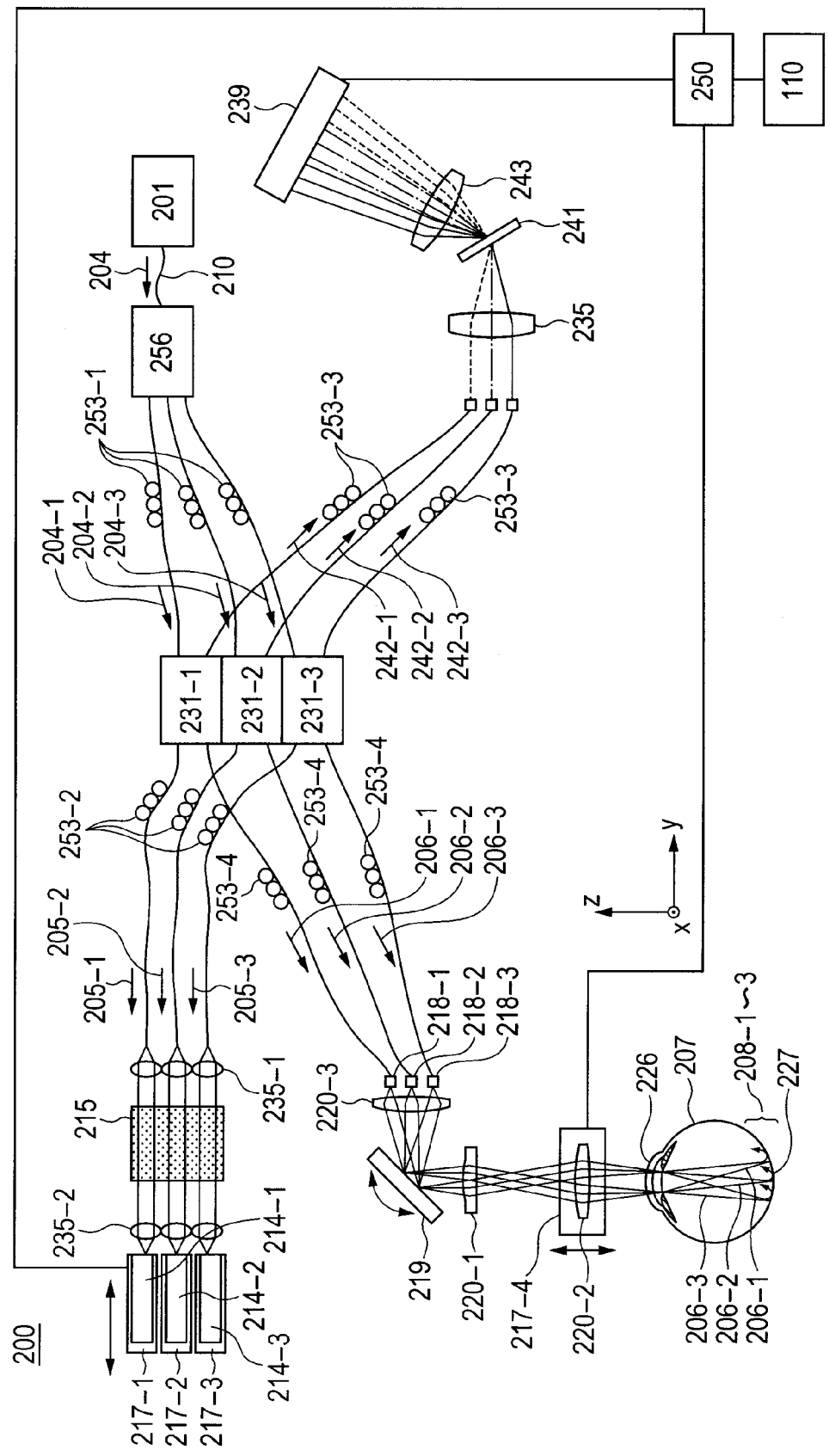
FIG. 2A is a diagram schematically illustrating an apparatus configuration.

The tomographic image photographing apparatus 200 is an apparatus for photographing a tomographic image of an eye as an object to be inspected in the present invention, and FIG. 2A illustrates a configuration of the tomographic image photographing apparatus 200 in this embodiment. The tomographic image photographing apparatus 200 constitutes a Michelson interferometer system as a whole as illustrated in FIG. 2A. The tomographic image photographing apparatus 200 in this embodiment is supposed to have three measuring light beams in the following description. The tomographic image photographing apparatus 200 corresponds to a photographing unit in the present invention, and the number of measuring light beams, which is three in this embodiment, only needs to be two or more. In addition, an interval in the sub scanning direction between the measuring light beams is appropriately determined in advance when the measuring light beams irradiate a fundus so that an operation of combining obtained tomographic images becomes easy.

Emerging light 204 that is emitted from a light source 201 is guided by a single mode fiber 210 to enter an optical coupler 256, and is split by the optical coupler 256 into three emerging light beams 204-1 to 204-3 propagating in a first optical path, a second optical path, and a third optical path, respectively. Further, each of the three emerging light beams 204-1 to 204-3 passes through a polarization controller 253-1, and is split by optical couplers 231-1 to 231-3 into reference light beams 205-1 to 205-3 and measuring light beams 206-1 to 206-3. Those three split measuring light beams 206-1 to 206-3 are reflected or scattered by individual measuring points of a retina 227 or the like of an eye to be inspected 207 as an object to be observed, and then are returned as return light beams 208-1 to 280-3. Then, the return light beams 208-1 to 280-3 are combined with the reference light beams 205-1 to 205-3 which have propagated reference light paths by the optical couplers 231-1 to 231-3, and become combined light beams 242-1 to 242-3. The combined light beams 242-1 to 242-3 are dispersed respectively for each wavelength by a transmission diffraction grating 241 and enter different regions of a line sensor 239. The line sensor 239 converts light intensity at each wavelength into a voltage by each sensor element, and a control unit 250 uses the signal to form a tomographic image of the eye to be inspected 207.

The reference light paths of the reference light 205 are now described. Each of the three reference light beams 205-1 to 205-3 split by the optical couplers 231-1 to 231-3 passes through the polarization controller 253-2 and is substantially collimated by a lens 235-1. Next, the reference light beams 205-1 to 205-3 pass through a dispersion compensation glass 215 and are condensed by a lens 235-2 onto mirrors 214-1 to 214-3, respectively. Then, the reference light beams 205-1 to 205-3 change the directions by the mirrors 214-1 to 214-3, respectively, and are directed again to the optical couplers 231-1 to 231-3. The reference light beams 205-1 to 205-3 pass through the optical couplers 231-1 to 231-3 and are guided to the line sensor 239. Note that, the dispersion compensation glass 215 is disposed for compensating for dispersion of the measuring light 206 propagating forward and backward between the eye to be inspected 207 and a scanning optical system with respect to the reference light 205. Note that, a typical diameter of an average eyeball of Japanese is supposed to be 23 mm. Further, electric stages 217-1 to 217-3 can move in a direction indicated by the arrow of FIG. 2A so that optical path lengths of the reference light beams 205-1 to 205-3 can be adjusted and controlled, respectively. Then, the electric stages 217-1 to 217-3 are controlled by the control unit 250. Herein, a position in the measuring light path which matches the reference light path in terms of the optical distance is referred to as a coherence gate. By moving the electric stages 217-1 to 217-3, the coherence gate can be adjusted so as to set a measurement range in a depth direction.

Next, a measuring light path of the measuring light 206 is described. Each of the measuring light beams 206-1 to 206-3 split by the optical couplers 231-1 to 231-3 passes through a polarization controller 253-4 and is substantially collimated by a lens 220-3 to enter a mirror of an XY scanner 219 constituting the scanning optical system. In FIG. 2A, for simple illustration, the XY scanner 219 is illustrated as one mirror. However, actually, two mirrors including an X-scan (main scan) mirror and a Y-scan (sub scan) mirror are disposed close to each other so that raster scan of the retina 227 in the direction perpendicular to the optical axis is performed. Those mirrors function as a scanning unit for scanning the plurality of measuring light beams in the main scanning direction and in the sub scanning direction. In addition, the center of each of the measuring light beams 206-1 to 206-3 is adjusted to be substantially the same as a rotation center of the mirror of the XY scanner 219 by adjusting the lenses 220-1, 220-3, and the like. The lenses 220-1 and 220-2 are optical systems for the measuring light beams 206-1 to 206-3 to scan the retina 227, and have a configuration in which the measuring light beams 206-1 to 206-3 scan the retina 227 with a fulcrum in a vicinity of a cornea 226. Each of the measuring light beams 206-1 to 206-3 forms an image at an arbitrary position on the retina.

In addition, an electric stage 217-4 can move in a direction indicated by the arrow of FIG. 2A so that a position of the accompanying lens 220-2 can be adjusted and controlled. By adjusting a position of the lens 220-2, each of the measuring light beams 206-1 to 206-3 can be condensed onto a desired layer of the retina 227 of the eye to be inspected 207 for performing observation. When the measuring light beams 206-1 to 206-3 enter the eye to be inspected 207, the measuring light beams 206-1 to 206-3 become the return light beams 208-1 to 208-3 after being reflected or dispersed by the retina 227, and pass through the optical couplers 231-1 to 231-3 to be guided to the line sensor 239. Note that, the electric stage 217-4 is controlled by the control unit 250. With the configuration described above, the three measuring light beams can be scanned at the same time.

Figure 2B:
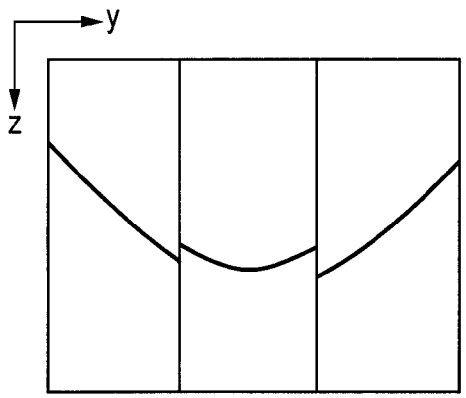
FIG. 2B is a diagram illustrating a tomographic image that is photographed.
Figure 2C:
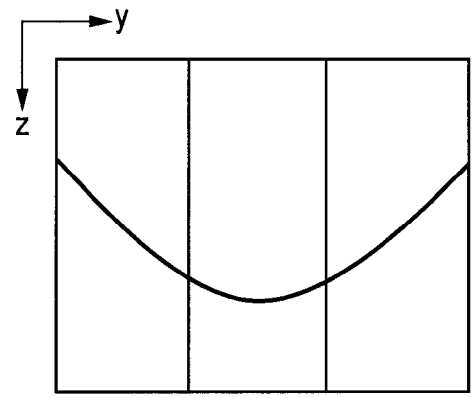
FIG. 2C is a diagram illustrating an example of a tomographic image after coherence gate adjustment.

FIG. 2B illustrates a YZ plane of a tomographic image obtained by photographing a model eye with three measuring light beams. FIG. 2B is a cross sectional view when the volume image is photographed with three measuring light beams. The model eye is a glass sphere having the same optical characteristic, size, and capacity as those of a living eye. When a plurality of measuring light beams is used for performing photographing, unless positions of the coherence gates of the individual measuring light beams are adjusted, as illustrated in FIG. 2B, a shape of the object to be inspected cannot be correctly restored. Therefore, in this embodiment, position relationship among three coherence gates is adjusted in advance so that a shape of the object to be inspected is restored as illustrated in FIG. 2C when a motionless object to be inspected such as the model eye is photographed.

For instance, if a depth resolution is 6 µm and the number of pixels of the spectroscope is 1,000, a measurable depth is 6×500=3 mm. If there is a deviation of several hundreds µm, a desired region may not be measured. Positions of the coherence gate are adjusted so as to eliminate the deviation, and an interference distance is set to a predetermined appropriate interval. Thus, data can be handled in the same manner as in measurement with a single measuring light beam. Note that, calibration of the depth resolution is performed so that when the coherence gates are moved by the same distance, the tomographic images move the same number of pixels. The depth resolution adjustment in the tomographic image is performed by zero-padding in which zeros are added to data of the spectroscope. In order to adjust positions of the coherence gates, an overlapping region among the measuring light beams is used. As another method, it is possible to perform scanning in a direction that enables to acquire the tomographic image of the YZ plane by one time of measurement so that the tomographic images can be connected without incompatibility. Information (correction value) necessary for correcting a deviation obtained from the measurement data is stored in a memory unit 112 for each tomographic image photographing apparatus.

Next, the image processing apparatus 110 is described. The image processing apparatus 110 includes an image acquiring unit 111, the memory unit 112, an image processing unit 113, and a display control unit 114. The image processing unit 113 includes a detection unit 131, an estimation unit 132, and an image deformation correction unit 133. The image acquiring unit 111 acquires a tomographic image photographed by the tomographic image photographing apparatus 200 (three-dimensional image constituted of a plurality of two-dimensional tomographic images) and stores the tomographic image in the memory unit 112. The detection unit 131 detects a layer such as a retina layer from the tomographic image stored in the memory unit 112. In other words, the detection unit 131 detects the retina layer from each of the plurality of tomographic images obtained by photographing the fundus at a predetermined timing among the plurality of tomographic images constituting the three-dimensional image. In this case, it is preferred that the detection unit 131 as an example of the detection unit judge whether the obtained structure has a normal layer structure or an abnormal layer structure for each layer in the obtained fundus image. In addition, the estimation unit 132 estimates the shape model through use of a result of the layers detected by the detection unit 131 in the plurality of tomographic images photographed at the same time. It is preferred that the estimation unit 132 as an example of the estimation unit estimate a fundus shape from a layer structure part that is detected to be a part having a normal layer structure by the detection unit 131. In addition, the image deformation correction unit 133 corrects the volume image deformation through use of the shape model estimated by the estimation unit 132. In other words, the image deformation correction unit 133 as an example of the correction unit corrects positional deviation between the plurality of tomographic images constituting the above-mentioned three-dimensional image based on the estimated fundus shape. It is preferred that the image deformation correction unit 133 correct a retina layer position in the tomographic image based on a value controlled by a control unit that controls the above-mentioned XY scanner 219. Note that, the above-mentioned tomographic image pickup apparatus 200 functions as an image acquiring unit that acquires the three-dimensional image of the fundus of the eye to be inspected in the present invention.

Figure 3A:
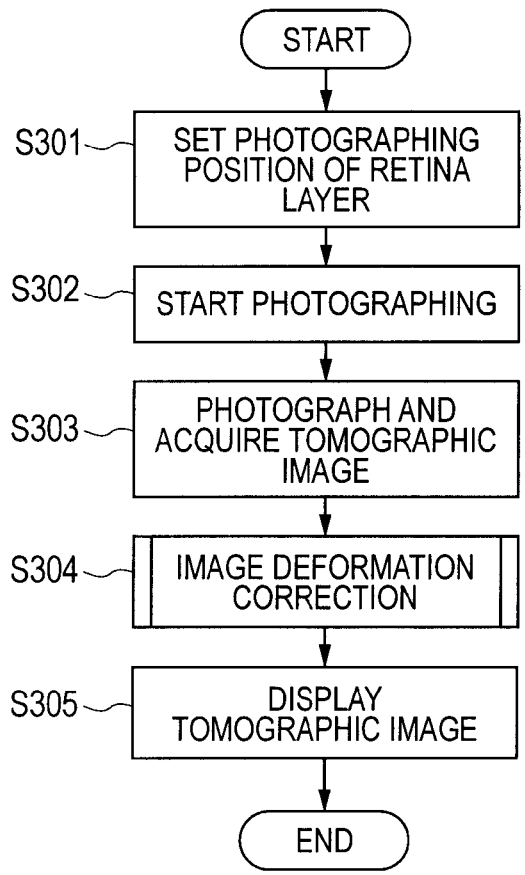
FIG. 3A is a flowchart illustrating a process flow in the image processing system.

Next, referring to FIG. 3A, a process procedure of the image processing system 100 of this embodiment is described.

(Step S301)

Figure 4A:
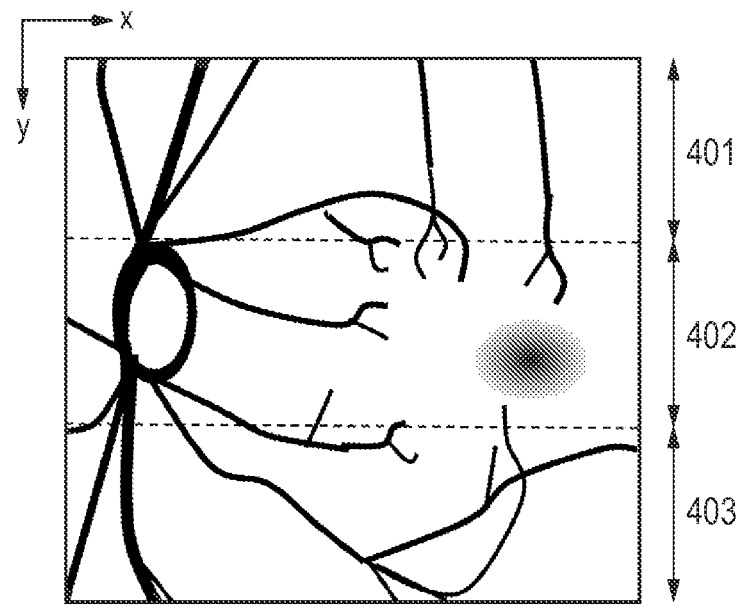
FIG. 4A is a diagram illustrating regions photographed with a plurality of measuring light beams.
Figure 4B:
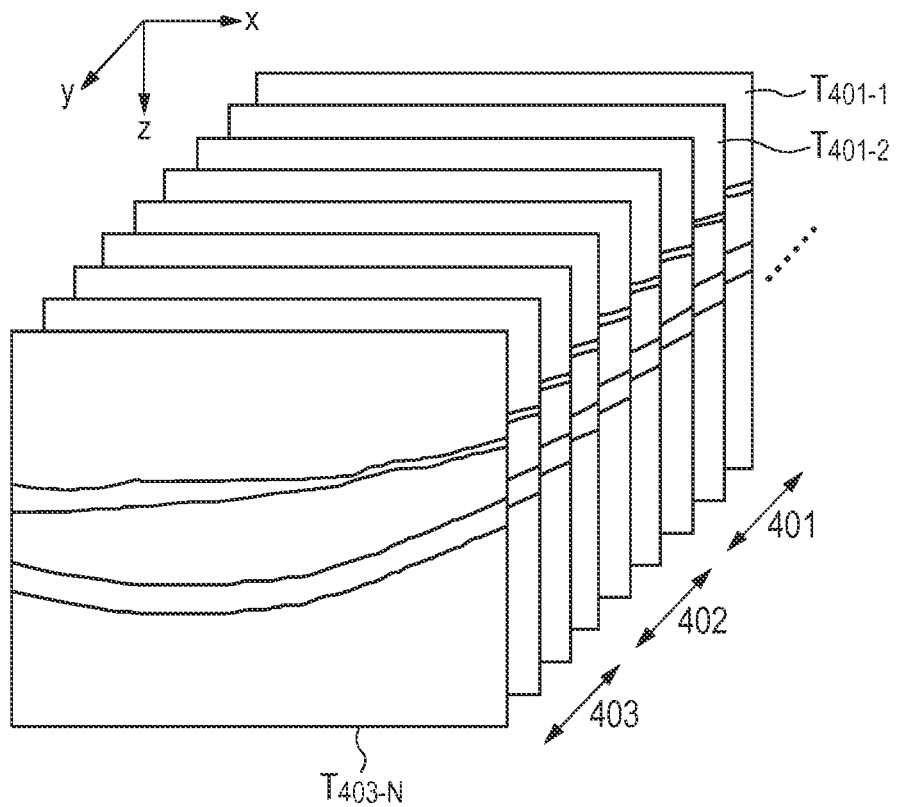
FIG. 4B is a diagram illustrating a volume image of a retina.

FIGS. 4A and 4B illustrate an example of photographing the eye to be inspected with a plurality of measuring light beams. FIG. 4A is a schematic diagram of a fundus illustrating a scan line, and FIG. 4B is a volume image of a retina photographed by the tomographic image photographing apparatus 200. With respect to the three measuring light beams, there are a first region 401 scanned by the measuring light beam 206-1, a second region 402 scanned by the measuring light beam 206-2, and a third region 403 scanned by the measuring light beam 206-3, which are indicated by the arrows. When N tomographic images are photographed with each measuring light, the tomographic images of the measuring light beams are tomographic images $T_{401-1}$, $T_{401-2}$, ... $T_{401-N}$ scanned by the measuring light beam 206-1, tomographic images $T_{402-1}$, ..., $T_{402-N}$ scanned by the measuring light beam 206-2, and tomographic images $T_{403-1}$, ..., $T_{403-N}$ scanned by the measuring light beam 206-3. Note that, part of regions photographed with neighboring measuring light beams may be overlapped, although not illustrated.

In Step S301, in order to photograph the retina layer, positions of the eye to be inspected in a plane direction (xy direction of FIG. 4A) and a depth direction (z direction of FIG. 4B) are adjusted. Herein, the adjustment of the position in the depth direction corresponds to adjustment of the coherent gate position for obtaining the tomographic image. Note that, in this embodiment, it is supposed that the positions of the coherence gates of the three measuring light beams move together while maintaining initially set position relationship.

(Step S302)

After the retina layer is adjusted to the position suitable for photographing in Step S301, photographing is started by an instruction from a photographing instruction unit (not shown) in Step S302.

(Step S303)

In Step S303, when the operator instructs to photograph, the XY scanner 219 constituting the scanning optical system performs raster scan of the retina 227 in the direction perpendicular to the optical axis. In FIG. 2A, for simple illustration, the XY scanner 219 is illustrated as a single mirror, but actually, two mirrors including the X-scan mirror and the Y-scan mirror are disposed close to each other so as to perform raster scan of the retina 227 in the direction perpendicular to the optical axis. Through the raster scan, the volume image of the retina is acquired. Then, the image acquiring unit 111 acquires the tomographic image photographed by the tomographic image photographing apparatus 200 and stored the tomographic image in the memory unit 112. This step corresponds to a photographing step in which the tomographic image of the fundus is photographed with a plurality of measuring light beams in the present invention.

(Step S304)

Figure 3B:
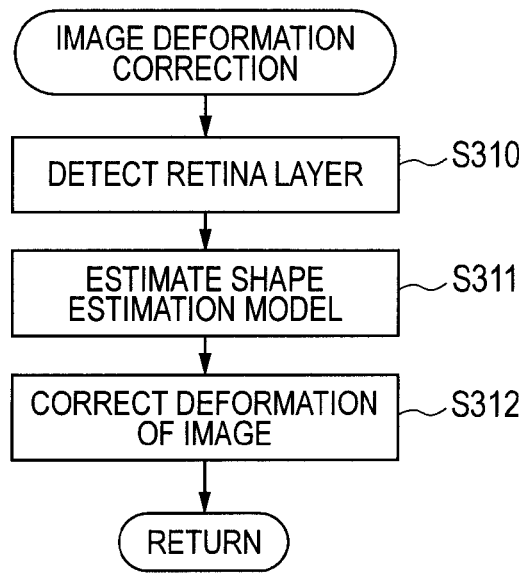
FIG. 3B is a diagram illustrating a subroutine performed in the flowchart illustrated in FIG. 3A.

In Step S304, the image processing unit 113 estimates the shape model and uses the shape model to perform volume image deformation correction. This process is described with reference to FIG. 3B.

(Step S310)

In Step S310, the detection unit 131 detects the retina layer from the tomographic image acquired in Step S303. The layer structure inside the retina layer includes an internal limiting membrane (ILM), a nerve fiber layer (NFL), a ganglion cell layer (GCL), an inner plexiform layer (IPL), an inner nuclear layer (INL), an outer plexiform layer (OPL), an outer nuclear layer (ONL), an external limiting membrane (ELM), a visual cell inner segment and outer segment junction (IS/OS), and a retinal pigment epithelium (RPE). It is sufficient that the detection unit 131 detects at least one of those layers, but the estimation by the shape model can be performed more easily if the IS/OS or the RPE is detected. The detection of a layer by the detection unit 131 corresponds to detection of a boundary between layers. For instance, by detecting an internal limiting membrane 1 at a boundary between the vitreous body and the retina, and a boundary between a nerve fiber layer 2 and a ganglion cell layer 3, the nerve fiber layer 2 is detected. Here, the detection unit 131 detects and judges whether the obtained layer structure is the normal layer structure or the abnormal layer structure, and provides the normal layer structure as data to be used when the estimation unit 132 estimates the fundus shape. This step corresponds to a detection step of detecting the retina layer or the like from the photographed fundus image in the present invention. Note that, the normal layer structure as used herein refers to a structure in which the layer that is usually to exist in the retina layer exists to have a usual thickness, and the abnormal layer structure as used herein refers to a structure in which a layer or a boundary to inherently exist cannot be obtained as a signal with correct intensity because of a disease, an injury, or congenital defect.

As to detection of the retina layer, a median filter and a Sobel filter are first used respectively for the tomographic image so as to generate images (hereinafter, referred to as a median image and a Sobel image). Next, a profile is generated from the converted median image and Sobel image for each A-scan. A brightness value profile is generated from the median image, and a gradient profile is generated from the Sobel image. Then, a peak in the profile generated from the Sobel image is detected. With reference to the profiles of the median image corresponding to before and after the detected peak or between peaks, the retina layer is detected.

A method of detecting the retina layer is not limited to the above-mentioned method, and the layer may be detected by a graph cut method, an active contour method, or the like.

(Step S311)

In Step S311, the estimation unit 132 uses information of the retina layer detected in Step S310 so as to estimate the shape model. This step corresponds to an estimation step of estimating the fundus shape based on the detected retina layer in the present invention.

Here, description is given of a case where model parameters of a second order curve and a second order curved surface are estimated as the shape model.

Figure 5A:
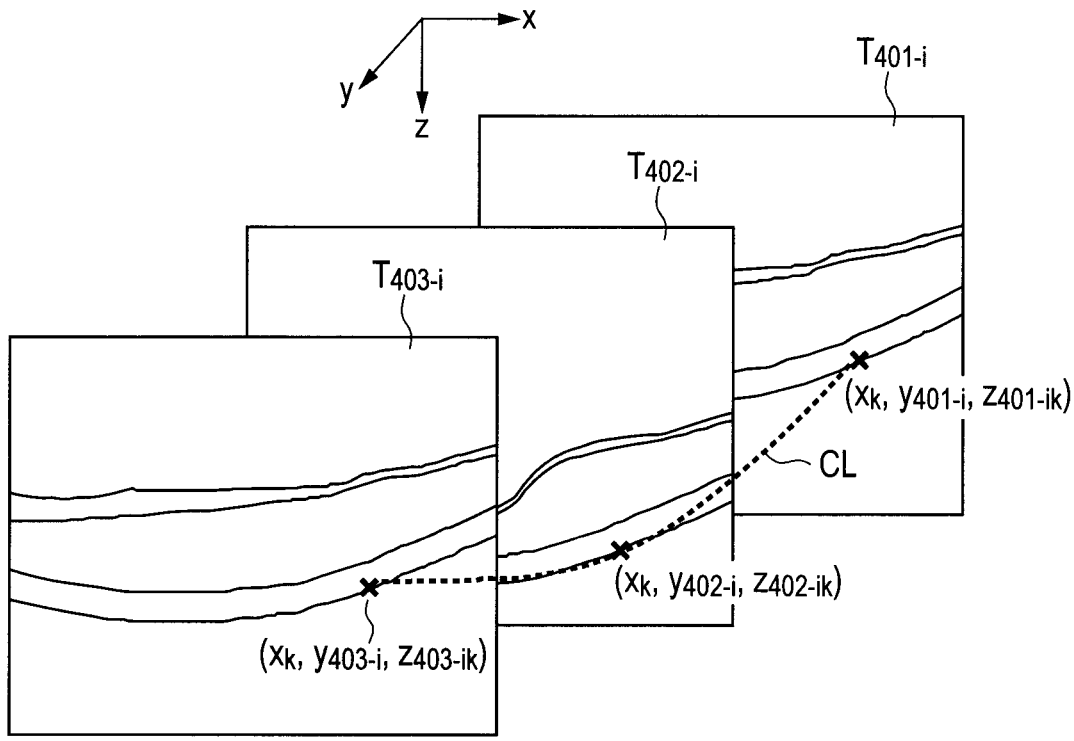
FIG. 5A is a diagram illustrating a method for image deformation correction.

First, referring to FIG. 5A, description is given of a case where a second order curve is used as the shape model. Here, at the same x coordinate of the tomographic images $T_{401-i}$, $T_{402-i}$, and $T_{403-i}$ obtained with the three measuring light beams photographed at the same time (referred to as time point i), the second order curve is estimated from the position of the retina layer detected in Step S310 (RPE in this embodiment). The "same time" in this embodiment means that the time from start to end of the scan for acquiring one tomographic image is the same, and means a time in which three tomographic images can be acquired in the case of the three measuring light beams. In FIG. 5A, a second order curve CL in $x_k$ coordinates is indicated by the dotted line. In FIG. 5A, in the case of the $x_k$ coordinates, the second order curve CL is estimated from sets of coordinates $(x_k, y_{401\text{-}i}, z_{401\text{-}ik})$, $(x_k, y_{402\text{-}i}, z_{402\text{-}ik})$, and $(x_k, y_{403\text{-}i}, z_{403\text{-}ik})$. Equation 1 shows an equation of the second order curve CL in the coordinate system of FIG. 5A. Parameters a, b, and c of the second order curve CL can be determined by calculating Equations 1 to 4. In Equation 2, "≈" means that both sides are nearly equal, and in Equation 3, "→min" means that the equation on the left side is to be minimized. This is an equation of a least squares method, and a partial differential is solved for each of a, b, and c so that normal equation of Equation 4 is obtained.

$$z = ay^2 + by + c \quad \text{[Equation 1]}$$

$$z_\alpha \approx a y_\alpha^2 + b y_\alpha + c, \ \alpha = 1, 2, 3 \quad \text{[Equation 2]}$$

$$J = \frac{1}{2} \sum_{\alpha=1}^{3} (z_\alpha - (a y_\alpha^2 + b y_\alpha + c))^2 \to \min \quad \text{[Equation 3]}$$

$$\begin{pmatrix} \sum_{\alpha=1}^{3} x_\alpha^4 & \sum_{\alpha=1}^{3} x_\alpha^3 & \sum_{\alpha=1}^{3} x_\alpha^2 \\ \sum_{\alpha=1}^{3} x_\alpha^3 & \sum_{\alpha=1}^{3} x_\alpha^2 & \sum_{\alpha=1}^{3} x_\alpha \\ \sum_{\alpha=1}^{3} x_\alpha^2 & \sum_{\alpha=1}^{3} x_\alpha & \sum_{\alpha=1}^{3} 1 \end{pmatrix} \begin{pmatrix} a \\ b \\ c \end{pmatrix} = \begin{pmatrix} \sum_{\alpha=1}^{3} x_\alpha^2 y_\alpha \\ \sum_{\alpha=1}^{3} x_\alpha y_\alpha \\ \sum_{\alpha=1}^{3} y_\alpha \end{pmatrix} \quad \text{[Equation 4]}$$

When the second order curve is used as the shape model, the model parameter is estimated by using a position coordinate of the retina layer at an arbitrary x coordinate from the tomographic images $T_{401\text{-}i}$, $T_{402\text{-}i}$, and $T_{403\text{-}i}$ photographed at the same time with the three measuring light beams. In this embodiment, the model parameter is estimated at an arbitrary x coordinate. However, it is possible to determine the parameter from a plurality of x coordinates and to use an average value of the parameters. Further, it is possible to estimate the model parameter by using the position coordinate of the retina layer at an arbitrary x coordinate from tomographic images $T_{401\text{-}j}$, $T_{402\text{-}j}$, and $T_{403\text{-}j}$ photographed at the same time at a time point different from the time point i (referred to as time point j) and to use an average value of the parameters determined at the time points i and j.

Figure 5B:
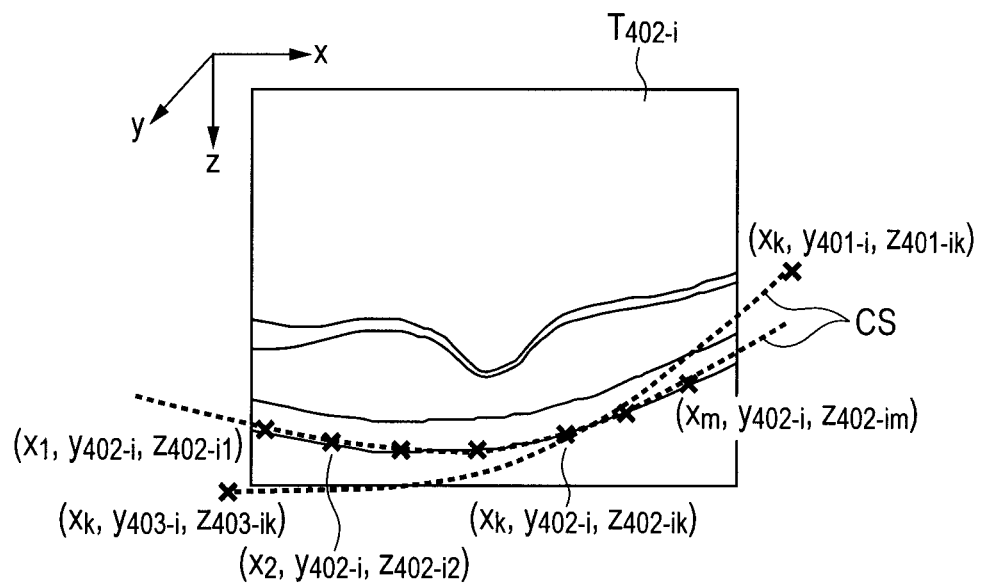
FIG. 5B is a diagram illustrating a case where a second order curved surface is used as a shape model for image deformation correction.

Next, description is given of a case where a second order curved surface is used as the shape model with reference to FIG. 5B. In the tomographic images $T_{401\text{-}i}$, $T_{402\text{-}i}$, and $T_{403\text{-}i}$ photographed at the same time (at the time point i) with the three measuring light beams, the second order curved surface is estimated from the position of the retina layer detected in Step S310 (RPE in this embodiment). In FIG. 5B, the tomographic image $T_{402\text{-}i}$ and a second order curved surface CS are illustrated. Note that, as to the second order curved surface CS, only ones on the tomographic image $T_{402\text{-}i}$ and on an $x_j$ coordinate are illustrated. In FIG. 5B, the second order curved surface CS is estimated from sets of coordinates $(x_1, y_{401\text{-}i}, z_{401\text{-}i\,1})$, $(x_2, y_{401\text{-}i}, z_{401\text{-}i\,2})$, ... $(x_m, y_{401\text{-}i}, z_{401\text{-}i\,m})$, $(x_1, y_{402\text{-}i}, z_{402\text{-}i\,1})$, $(x_2, y_{402\text{-}i}, z_{402\text{-}i\,2})$, ... $(x_m, y_{402\text{-}i}, z_{402\text{-}i\,m})$, $(x_1, y_{403\text{-}i}, z_{403\text{-}i\,1})$, $(x_2, y_{403\text{-}i}, z_{403\text{-}i\,2})$, ... and $(x_m, y_{403\text{-}i}, z_{403\text{-}i\,m})$. Equation 5 shows an equation of the second order curved surface in the coordinate system of FIG. 5B. Parameters a, b, c, d, e, and f of the second order curved surface CS can be determined by calculating Equations 5 to 8. In Equations 6 to 8, M represents the number of coordinate points for determining the second order curved surface.

$$z = ax^2 + bxy + cy^2 + dx + ey + f \quad \text{[Equation 5]}$$

$$z_\alpha \approx a x_\alpha^2 + b x_\alpha y_\alpha + c y_\alpha^2 + d x_\alpha + e y_\alpha + f, \ \alpha = 1, 2, \ldots, M \quad \text{[Equation 6]}$$

$$J = \frac{1}{2} \sum_{\alpha=1}^{M} (z_\alpha - (a x_\alpha^2 + b x_\alpha y_\alpha + c y_\alpha^2 + d x_\alpha + e y_\alpha + f))^2 \to \min \quad \text{[Equation 7]}$$

$$\begin{pmatrix} \sum_{\alpha=1}^{M} x_\alpha^4 & \sum_{\alpha=1}^{M} x_\alpha^3 y_\alpha & \sum_{\alpha=1}^{M} x_\alpha^2 y_\alpha^2 & \sum_{\alpha=1}^{M} x_\alpha^3 & \sum_{\alpha=1}^{M} x_\alpha^2 y_\alpha & \sum_{\alpha=1}^{M} x_\alpha^2 \\ \sum_{\alpha=1}^{M} x_\alpha^3 y_\alpha & \sum_{\alpha=1}^{M} x_\alpha^2 y_\alpha^2 & \sum_{\alpha=1}^{M} x_\alpha y_\alpha^3 & \sum_{\alpha=1}^{M} x_\alpha^2 y_\alpha & \sum_{\alpha=1}^{M} x_\alpha y_\alpha^2 & \sum_{\alpha=1}^{M} x_\alpha y_\alpha \\ \sum_{\alpha=1}^{M} x_\alpha^2 y_\alpha^2 & \sum_{\alpha=1}^{M} x_\alpha y_\alpha^3 & \sum_{\alpha=1}^{M} y_\alpha^4 & \sum_{\alpha=1}^{M} x_\alpha y_\alpha^2 & \sum_{\alpha=1}^{M} y_\alpha^3 & \sum_{\alpha=1}^{M} y_\alpha^2 \\ \sum_{\alpha=1}^{M} x_\alpha^3 & \sum_{\alpha=1}^{M} x_\alpha^2 y_\alpha & \sum_{\alpha=1}^{M} x_\alpha y_\alpha^2 & \sum_{\alpha=1}^{M} x_\alpha^2 & \sum_{\alpha=1}^{M} x_\alpha y_\alpha & \sum_{\alpha=1}^{M} x_\alpha \\ \sum_{\alpha=1}^{M} x_\alpha^2 y_\alpha & \sum_{\alpha=1}^{M} x_\alpha y_\alpha^2 & \sum_{\alpha=1}^{M} y_\alpha^3 & \sum_{\alpha=1}^{M} x_\alpha y_\alpha & \sum_{\alpha=1}^{M} y_\alpha^2 & \sum_{\alpha=1}^{M} y_\alpha \\ \sum_{\alpha=1}^{M} x_\alpha^2 & \sum_{\alpha=1}^{M} x_\alpha y_\alpha & \sum_{\alpha=1}^{M} y_\alpha^2 & \sum_{\alpha=1}^{M} x_\alpha & \sum_{\alpha=1}^{M} y_\alpha & \sum_{\alpha=1}^{M} 1 \end{pmatrix} \begin{pmatrix} a \\ b \\ c \\ d \\ e \\ f \end{pmatrix} = \begin{pmatrix} \sum_{\alpha=1}^{M} x_\alpha^2 z_\alpha \\ \sum_{\alpha=1}^{M} x_\alpha y_\alpha z_\alpha \\ \sum_{\alpha=1}^{M} y_\alpha^2 z_\alpha \\ \sum_{\alpha=1}^{M} x_\alpha z_\alpha \\ \sum_{\alpha=1}^{M} y_\alpha z_\alpha \\ \sum_{\alpha=1}^{M} z_\alpha \end{pmatrix} \quad \text{[Equation 8]}$$

When the second order curved surface is used as the shape model, it is possible to estimate the model parameter by using a position of the retina layer from the tomographic images $T_{401-i}$, $T_{402-i}$, and $T_{403-i}$ photographed at the same time with the three measuring light beams. As for the second order curved surface too, it is possible to estimate the model parameter by using the position coordinate of the retina layer from the tomographic image $T_{401-j}$, $T_{402-j}$, and $T_{403-j}$ photographed at the same time at a time different from the time point i (referred to time point j), and to use an average value of the parameters determined at the time points i and j.

Here, the case where the model parameters of the second order curve and the second order curved surface are estimated is described above, but the shape model is not limited thereto. It is possible to use an n-th order curve or an n-th order curved surface. Note that, an example of the least squares method is described above as a method of determining the shape model, but the method of determining the shape model is not limited to this method. It is possible to use a robust estimation method such as M estimation, least median of squares (LMedS), or random sample consensus (RANSAC) to determine the shape model.

(Step S312)

Figure 6A:
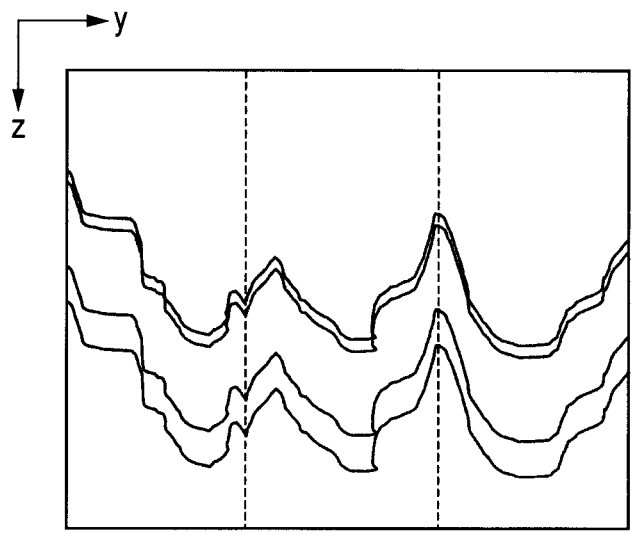
FIG. 6A is a diagram illustrating an example of an image before the deformation correction is performed.
Figure 6B:
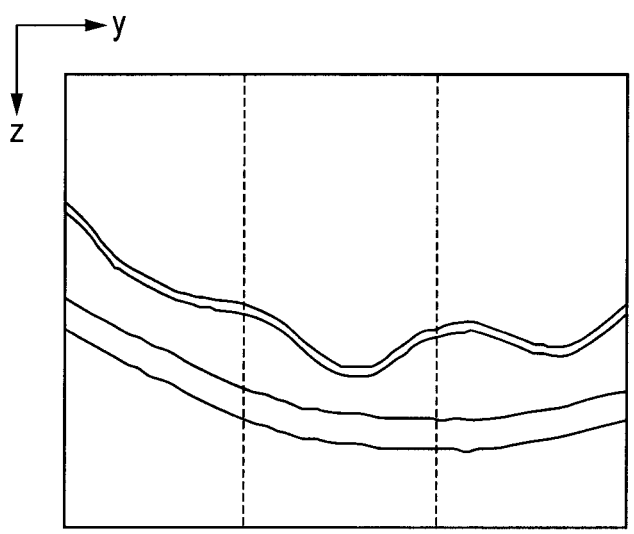
FIG. 6B is a diagram illustrating an example of an image after the deformation correction is performed by using the shape model.

In Step S312, the volume image deformation correction is performed by using the shape model estimated in Step S311. This step corresponds to an image deformation correction step of correcting positional deviation between the tomographic images based on the estimated fundus shape in the present invention. Here, a position of the tomographic image i is exemplified and described. In the tomographic image i, a value of the shape model $z_{Model\ i}$ is determined. Therefore, a difference $\Delta z_i$ between the value of the $z_{Model\ i}$ determined in the shape model and the coordinate position $Z_{RPE\ i}$ of the retina layer of the tomographic image (RPE in this embodiment) is the correction value in the depth direction of each tomographic image. Therefore, in Step S312, the tomographic image position correction in the depth direction is performed based on the determined correction value for each tomographic image. FIGS. 6A and 6B illustrate an example of a case where the volume image deformation correction is performed by using the shape model. FIGS. 6A and 6B illustrate the YZ plane of the tomographic image obtained by photographing the retina with three measuring light beams. FIG. 6A illustrates the YZ plane of the volume image before the deformation correction, and FIG. 6B illustrates the YZ plane of the volume image after the deformation correction by using the shape model. As illustrated in FIGS. 6A and 6B, through use of the shape model, the shape of the retina layer can be restored. Note that, when the image of FIG. 6B is generated from the image of FIG. 6A, the image is shifted in the depth direction according to a correction value calculated for each tomographic image. Therefore, a blank region is generated in the shifted part. A value calculated from the region before the shift is substituted into the blank region. As a method for the calculation, a bi-linear method, a bi-cubic method, or the like is used, for example. Alternatively, instead of interpolation, it is possible to substitute a specific value such as zero or a maximum value of the image (65,535 in the case of a 16-bit image).

(Step S305)

In Step S305, the display control unit 114 displays the volume image (not shown) after the image deformation correction in Step S304 on a display unit. Note that, if not only displaying the image but also retina layer thickness measurement or the like is performed, it is possible to measure the layer thickness from a result of the detection of the determined retina layer in Step S310, and to superimpose and display the result of the detection as a boundary line on the tomographic image. Further, it is possible to generate and display a map of thickness.

According to the configuration described above, when the volume image is photographed with a plurality of measuring light beams, the retina layer is detected from a plurality of tomographic images obtained by photographing spatially separated points at the same time, and the shape model is estimated by using the detected retina layer. Then, through use of the shape model, the volume image deformation is corrected so that the volume image deformation can be corrected accurately even if the object to be inspected moves during the scanning by the tomographic image photographing apparatus.

Second Embodiment

In the first embodiment described above, the parameter of the shape model is determined from an arbitrary set of the tomographic images (one set is the three tomographic images in a second embodiment of the present invention) when the shape model is determined. Then, as for other tomographic image sets, alignment in the depth direction is performed according to a difference between the determined shape model and the retina layer position of each tomographic image. In this embodiment, description is given of a case where the shape model parameter and a parallel movement amount parameter in each tomographic image set are determined so as to correct the volume image deformation by using all sets of the tomographic images (N sets in this embodiment). In this embodiment, the case where the shape model is the second order curved surface is described. Then, as a method of determining the parameter, description is given of a method in which the shape model parameter and the parallel movement amount parameter are first determined in each tomographic image set, and through use of the parameters as initial values, the entire parameters are determined. Note that, this embodiment corresponds to Steps S311 and S312 in the first embodiment.

Hereinafter, description is given of a method in which the model shape is determined in each tomographic image set (the sets are represented by $G_1, G_2, \ldots G_N$), and through use of the model shape as initial values, the entire parameters are determined. FIG. 7 illustrates an example of each tomographic image set. A plurality of tomographic images photographed at the same time is divided into a plurality of sets, each of which includes a plurality of tomographic images photographed at the same time. Each set for which the fundus shape is estimated is includes the three tomographic images photographed at the same time with three measuring light beams. In this embodiment, N tomographic images are photographed with each of the three measuring light beams. Therefore, there are N sets of the tomographic images.

The equations are shown as Equations 9 to 11. Here, Equation 11 is determined by using the parameters determined by Equations 9 and 10 as initial values. Equation 9 is an equation for calculating the shape model parameter and the parallel movement amount for each tomographic image set, and Equation 10 is an equation for determining an average value of the shape model parameters determined by Equation 9.

Equation 9 is a non-linear minimization problem, and hence each parameter can be determined by a quasi-Newton method, a conjugate gradient method, a Powell method, or the like. As the initial values for solving Equation 9, an average shape model is generated in advance, and parameters a, b, c, d, e, and f of the average shape model and the center of the volume image are given as the initial values of the parallel movement amounts tx and ty. Herein, the average shape model refers to a model generated from the shape model of the plurality of retina layers. As a generation method, the retina layer is detected automatically or manually with respect to the plurality of retina layer data. Then, by calculating an average of the coordinate values while adjusting each detection result to a reference position, the average shape model can be determined. In Equations 9 and 11, suffixes of $x_{G1\alpha}, y_{G1\alpha}, z_{G1\alpha}$. indicate α-th coordinate values in the tomographic image sets ($G_1, G_2, \ldots$ and $G_N$), and M represents the number of coordinate points when the second order curved surface is determined.

G1:

$$J = \frac{1}{2}\sum_{\alpha=1}^{M}(z_{G1\alpha} - (a_1(x_{G1\alpha} - tx_1)^2 + b_1(x_{G1\alpha} - tx_1)(y_{G1\alpha} - ty_1) + c_1(y_{G1\alpha} - ty_1)^2 + d_1(x_{G1\alpha} - tx_1) + e_1(y_{G1\alpha} - ty_1) + f_1))^2 \to \min$$ [Equation 9]

G2:

$$J = \frac{1}{2}\sum_{\alpha=1}^{M}(z_{G2\alpha} - (a_2(x_{G2\alpha} - tx_2)^2 + b_2(x_{G2\alpha} - tx_2)(y_{G2\alpha} - ty_2) + c_2(y_{G2\alpha} - ty_2)^2 + d_2(x_{G2\alpha} - tx_2) + e_2(y_{G2\alpha} - ty_2) + f_2))^2 \to \min$$ [Equation 10]

GN:

$$J = \frac{1}{2}\sum_{\alpha=1}^{M}(z_{GN\alpha} - (a_N(x_{GN\alpha} - tx_N)^2 + b_N(x_{GN\alpha} - tx_N)(y_{GN\alpha} - ty_N) + c_N(y_{GN\alpha} - ty_N)^2 + d_N(x_{GN\alpha} - tx_N) + e_N(y_{GN\alpha} - ty_N) + f_N))^2 \to \min$$ [Equation 11]

$$a_{init} = \frac{1}{N}\sum_{i=1}^{N}a_i,\ b_{init} = \frac{1}{N}\sum_{i=1}^{N}b_i,\ c_{init} = \frac{1}{N}\sum_{i=1}^{N}c_i,$$

$$d_{init} = \frac{1}{N}\sum_{i=1}^{N}d_i,\ e_{init} = \frac{1}{N}\sum_{i=1}^{N}e_i,\ f_{init} = \frac{1}{N}\sum_{i=1}^{N}f_i$$ [Equation 12]

Equation 11 is an equation for determining the shape model and the parallel movement amount of the entire volume image. The value determined by Equation 10 is used as an initial value of the shape model parameter in Equation 11. Then, parameters $tx_1, \ldots tx_N$, and $ty_1, \ldots ty_N$ of the parallel movement amount determined by Equation are used as initial values of the parallel movement amount parameter in Equation 11. Equation 11 is also a non-linear minimization problem similarly to Equation 9, and hence the parameters (a, b, c, d, e, f, $tx_1 \ldots tx_N$, and $ty_1, \ldots ty_N$) can be determined by the quasi-Newton method, the conjugate gradient method, the Powell method, or the like.

$$J = \frac{1}{2}\sum_{\alpha=1}^{M}(z_{G1\alpha} - (a(x_{G1\alpha} - tx_1)^2 + b(x_{G1\alpha} - tx_1)(y_{G1\alpha} - ty_1) + c(y_{G1\alpha} - ty_1)^2 +$$ [Equation 13]

-continued
$$d(x_{G1\alpha} - tx_1) + e(y_{G1\alpha} - ty_1) + f))^2 +$$

$$\frac{1}{2}\sum_{\alpha=1}^{M}(z_{G2\alpha} - (a(x_{G2\alpha} - tx_2)^2 +$$

$$b(x_{G1\alpha} - tx_2)(y_{G1\alpha} - ty_2) + c(y_{G1\alpha} - ty_2)^2 +$$

$$d(x_{G1\alpha} - tx_2) + e(y_{G1\alpha} - ty_2) + f))^2 + \cdots +$$

$$\frac{1}{2}\sum_{\alpha=1}^{M}(z_{GI\alpha} - (a(x_{GI\alpha} - tx_N)^2 +$$

$$b(x_{GI\alpha} - tx_N)(y_{GI\alpha} - ty_N) + c(y_{GI\alpha} - ty_N)^2 +$$

$$d(x_{GI\alpha} - tx_N) + e(y_{GI\alpha} - ty_N) + f))^2 \to \min$$

In this embodiment, description is given of a method of determining the parameters (a, b, c, d, e, f, $tx_1, \ldots tx_N$, and $ty_1, \ldots ty_N$), in which the shape model parameter and the parallel movement amount parameter in each tomographic image set are determined by Equations 9 and 10, and through use of the result as initial values, the entire parameters are determined by Equation 11. However, the method of giving the initial values for determining the entire parameters is not limited to this method. For instance, it is possible to determine Equation by using the shape model parameter and the parallel movement amount determined in the first embodiment as the initial values instead of Equations 9 and 10. In addition, it is possible to determine Equation 11 by using the parameter of the average shape model as the initial values instead of Equations 9 and 10.

According to the configuration described above, the shape model parameter and the parallel movement amount parameter in each tomographic image set are determined by using the all sets of the tomographic images (N sets in this embodiment), and hence the shape model can be estimated robustly. Then, by correcting the volume image deformation through use of the shape model, the volume image deformation can be corrected accurately even if the object to be inspected moves during the scan by the tomographic image photographing apparatus.

Third Embodiment

Figure 8:
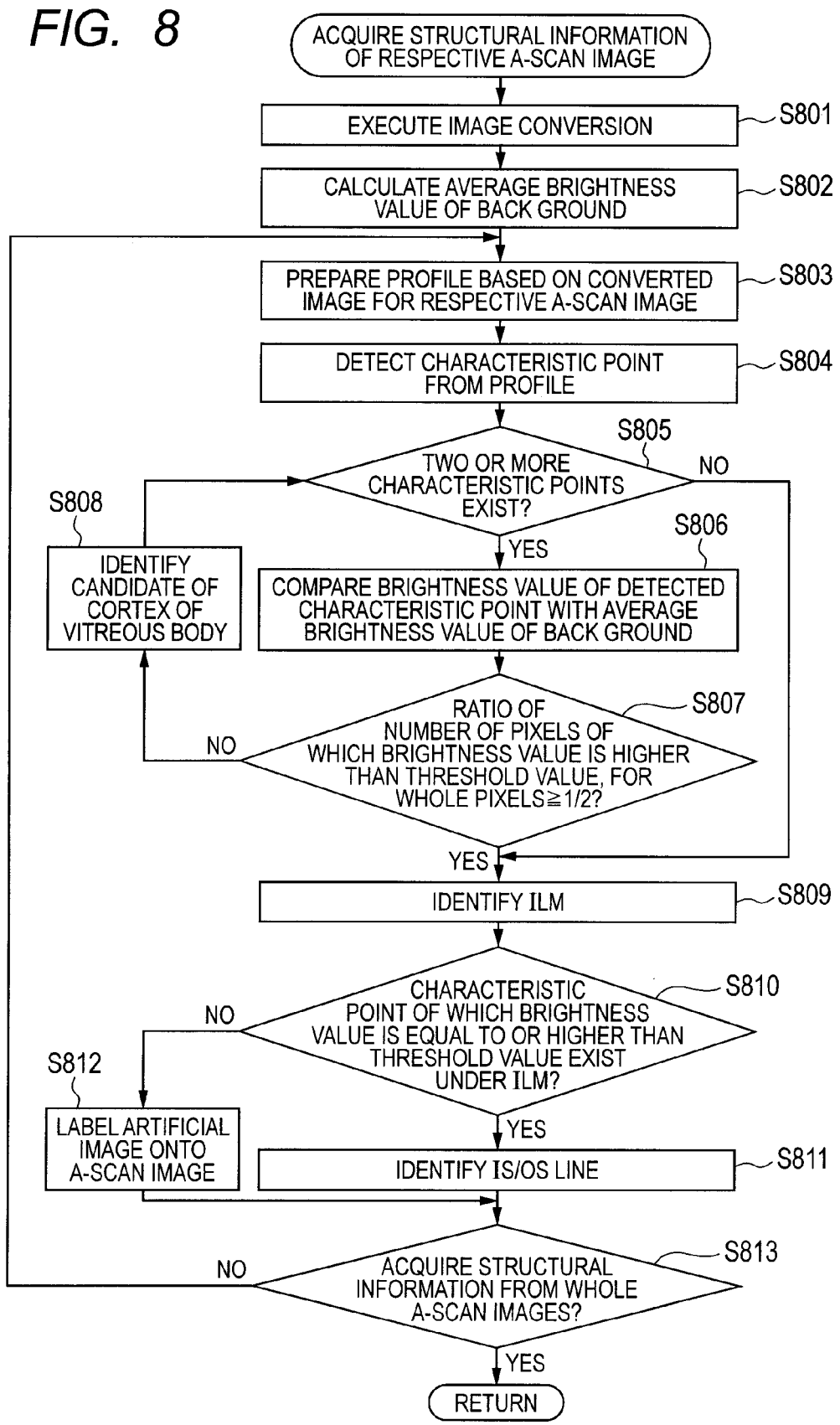
FIG. 8 is a flowchart illustrating a process flow in a detection unit.

In the first and second embodiments described above, the entire retina layer is detected, and the shape model is estimated by using an arbitrary coordinate point or the detected entire coordinate point data. In a third embodiment of the present invention, there is described a case where a coordinate point to be used for estimating the shape model is selected, and the shape of the object to be inspected is restored by using the selected coordinate point. Hereinafter, with reference to FIG. 8, a process procedure of the detection unit 131 in this embodiment is described.

(Step S801)

In Step S801, image conversion of a tomographic image is performed. In this embodiment, a median filter and a Sobel filter are applied to the tomographic image so as to generate a median image and a Sobel image, respectively. In this embodiment, a pixel value becomes larger as a signal intensity becomes higher, while the pixel value becomes smaller as the signal intensity becomes lower.

In this embodiment, the Sobel filter has a directional property in which a boundary from a low brightness value to a high brightness value is emphasized, when viewed from a shallow direction in the A-scan image (upper side of the image). The reason is as follows. In the present invention, when a retina layer structure is changed, used as structural information for identifying a cause of the change are the ILM, the IS/OS line, position information of the cortex of vitreous body in each A-scan image, and presence or absence of a false image are used. In the retina layer structure, the ILM and the cortex of vitreous body are a boundary between the vitreous body having a low brightness value and a retinal tissue having a relatively high brightness value, and the IS/OS line also contacts with a tissue having a relatively low brightness in the shallow direction. In addition, if the false image exists, the brightness under the IS/OS line is decreased. Therefore, it is possible to judge presence or absence of the false image from the pixel value in the Sobel image. In other words, by providing the above-mentioned directional property, the ILM, the IS/OS line, and the cortex of vitreous body are more emphasized, and further it is possible to judge presence or absence of the false image. Note that, the cortex of vitreous body is handled as a candidate of cortex of vitreous body in a retina layer structural information acquiring process, because a final identifying process is performed after the retina layer structural information acquiring process.

(Step S802)

In Step S802, an average brightness value of background (vitreous body) is calculated by using the median image generated in Step S801. In this embodiment, a binarization process is first performed on the median image by a P-tile method so that a background region is identified. Next, an average value of brightness values of the median image in the background region is calculated.

The binarization process by the P-tile method is a method in which a histogram of the image to be processed is generated and is accumulated from the highest or lowest brightness value, and hence a brightness value reaching a predetermined ratio P is set as a threshold value to perform the binarization. In this embodiment, because a ratio of the retina region in the image is substantially known, the P value is empirically set to 30 percent from the highest brightness value so as to perform the binarization process. Pixels having brightness values of the threshold value or lower are identified as background pixels.

After identifying the background pixels, a brightness value of the median image in the background pixels is referred to calculate the average brightness value of the background.

(Step S803)

In Step S803, a profile is prepared from the converted image generated in Step S801. In this embodiment, the profile is prepared from both the median image and the Sobel image for each A-scan image. By preparing the profile from the median image, it is possible to obtain an effect of suppressing a noise that becomes a problem particularly in the tomographic image, and hence a tendency of the brightness value can be more easily grasped. In addition, by preparing the profile from the Sobel image, it is possible to obtain an effect of easily detecting a candidate point of the retina layer boundary in identifying the retina layer boundary in the later stage. In addition, it is not always necessary to prepare the profile from these converted images. It is sufficient that an edge having a predetermined intensity can be detected from an original image or other converted image.

(Step S804)

In Step S804, a maximum point (hereinafter, referred to as a peak) is detected from the profile prepared in Step S803. In this embodiment, a peak in the profile prepared from the Sobel image is detected. In the detection, a threshold value determined empirically or based on image information is used. In a retina, many signals are reflected or scattered under the ILM, under the IS/OS line, and by the cortex of vitreous body. Therefore, by using the Sobel filter having the directional property of emphasizing the boundary from a low brightness value to a high brightness value when viewed from the shallow direction described above in Step S801, the ILM, the IS/OS line, and the cortex of vitreous body are easily detected as a strong edge. Other than these layers, there is no edge detected by the Sobel filter having this directional property except for a lesion portion. Therefore, by adjusting the threshold value, the ILM, the IS/OS line, and the candidate of cortex of vitreous body can be extracted with higher priority.

(Step S805)

In Step S805, peaks detected in Step S804 are counted, and the process is branched based on the count. In this embodiment, when there exist two or more peaks that are not identified as the retina layer boundary or the candidate of cortex of vitreous body in this step input (Yes in Step S805), two peaks are selected in order from the shallow direction in the A-scan image. Then, the two peaks are regarded as a first peak and a second peak, and the process proceeds to Step S806. In addition, if one peak exists (No in Step S805), a largest peak is regarded as a first peak, and the process proceeds to Step S809.

(Step S806)

In Step S806, the profile of the median image between two peaks selected in Step S805 is compared with the average brightness value of the background. In this embodiment, first, with respect to pixels between the first peak and the second peak, a threshold value is set, which is obtained by multiplying a coefficient of 1.2 to the average brightness value of the background calculated in Step S802. Next, a ratio of the number of pixels having a brightness value larger than this threshold value to the total number of pixels between the peaks is calculated.

Note that, this coefficient is empirically determined, and is not limited to this. For instance, it is possible to determine the coefficient dynamically from image information using a ratio between the average brightness value of the background and an average brightness value in the region other than the background (region of the threshold value or larger in the binarization process).

(Step S807)

In Step S807, the process is branched based on the ratio calculated in Step S806. In this embodiment, when the calculated ratio is smaller than ½ (No in Step S807), it is judged that the region between the peaks is the background, and the process proceeds to Step S808. When the calculated ratio is ½ or larger (Yes in Step S807), it is judged that there is the retinal tissue between the peaks, and the process proceeds to Step S809.

Note that, in this embodiment, whether the region is the retinal tissue or the background is judged from the ratio of pixels having the threshold value or larger, but this should not be interpreted as a limitation. For instance, it is possible to calculate a characteristic amount from the profile and to perform the judgment using an identifier with the characteristic amount as an input.

(Step S808)

In Step S808, one of the peaks is identified as a candidate of cortex of vitreous body. In this embodiment, as to the first peak and second peak judged to have the background therebetween in Step S807, if the cortex of vitreous body is peeled off, the first peak is identified as a candidate of cortex of vitreous body because there is the background thereunder. Then, the process returns to Step S805, and two peaks including the second peak are selected again.

(Step S809)

In Step S809, one of the peaks is identified as the ILM. In this embodiment, as to the first peak and second peak judged to have the retinal tissue therebetween in Step S807, the first peak is identified as the ILM because the ILM exists on the upper end of the retinal tissue. In addition, also when the process is branched from Step S805, the first peak is identified as the ILM.

(Step S810)

In Step S810, it is checked whether or not there exists a characteristic point having a value of the threshold value or larger in the deeper direction (lower part in the image) on the same A-scan image than the ILM identified in Step S809. In this embodiment, a value obtained by multiplying a coefficient of 0.8 to the peak value of the ILM identified on the same A-scan image is set as the threshold value. It is checked whether or not there exists a peak of this threshold value or larger in the deeper direction than the ILM. When a peak exists, (Yes in Step S810), the process proceeds to Step S811. If no peak exists (No in Step S810), the process proceeds to Step S812.

Note that, this threshold value is empirically determined and should not be interpreted as a limitation. For instance, instead of the peak value, it is possible to use a distance between peaks.

(Step S811)

In Step S811, a peak having a value of the threshold value or larger set in Step S810 is identified as the IS/OS line. If there are a plurality of peaks having a value of the threshold value or larger, a peak existing at the shallowest position among the peaks having a value of the threshold value or larger is identified as the IS/OS line in this embodiment.

(Step S812)

In Step S812, the A-scan image is labeled "false image" because the IS/OS line is not identified.

(Step S813)

In Step S813, it is checked whether or not the structural information is acquired from all the A-scan images. When the process is performed for all the A-scan images (Yes in Step S813), the process is finished. When there remains the A-scan image in which the structural information is not yet acquired (No in Step S813), the process returns to Step S803.

In this way, a tissue between peaks is judged, and based on the result, structural information of the retina layer is acquired. Thus, it is possible to reduce errors of the structural information. The ILM is identified in every A-scan image. On the other hand, there also exists the A-scan image in which the IS/OS line cannot be identified. As described above in Step S812, such A-scan image is labeled "false image".

The estimation unit 132 estimates the shape model from the detection result of the retina layer in the A-scan image which is not labeled as "false image". Note that, a method of estimating the shape model is as described above in the first and second embodiments.

According to the configuration described above, the shape model can be estimated accurately by selecting the coordinate point used for estimating the shape model. Therefore, the volume image deformation can be accurately corrected.

Fourth Embodiment

In the first embodiment described above, coherence gate positions of the three measuring light beams are adjusted in advance so that the shape of the object to be inspected is restored when the motionless object to be inspected such as a model eye is photographed. Then, there is described an example in which the three measuring light beams operate in conjunction with one another when the coherence gate position is changed. In this embodiment, there is described a case where the shape of the object to be inspected is restored when the coherence gate positions are changed independently by individual measuring light beams.

FIG. 9 is a diagram illustrating a configuration of an image processing system 900 including an image processing apparatus 910 according to this embodiment. As illustrated in FIG. 9, the image processing apparatus 910 includes the image acquiring unit 111, a memory unit 912, an image processing unit 915, the display control unit 114, the detection unit 131, the estimation unit 132, the image deformation correction unit 133, and a correction unit 934. Among them, description of the units having the same functions as those in the first embodiment described above is omitted here.

The memory unit 912 stores the movement amount in which each coherence gate position is adjusted independently from the coherence gate position in a position relationship for correctly restoring the shape of the object to be inspected.

The correction unit 934 corrects a position in the depth direction (Z direction) of each measuring light beam from the movement amount independently adjusted for restoring the shape of the object to be inspected.

Hereinafter, with reference to FIGS. 10A, 10B, and 11A to 11C, a process procedure of the image processing system 900 of this embodiment is described. Note that, steps other than Steps S1001, S1004, and S1011 are the same as those in the first embodiment, and therefore description thereof is omitted.

(Step S1001)

Figure 11A:
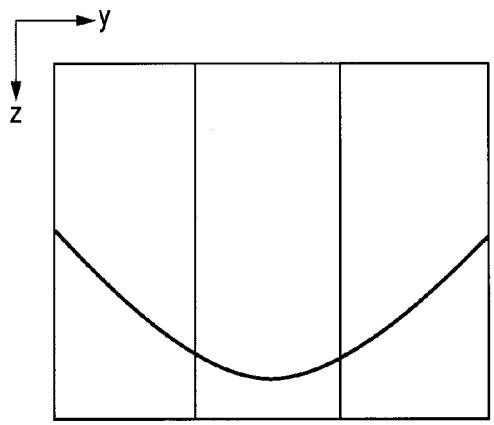
FIGS. 11A, 11B and 11C are diagrams illustrating a movement of a coherence gate position of the plurality of measuring light beams.
Figure 11B:
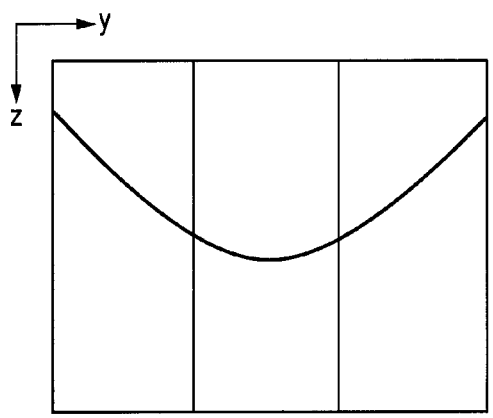
Figure 11C:
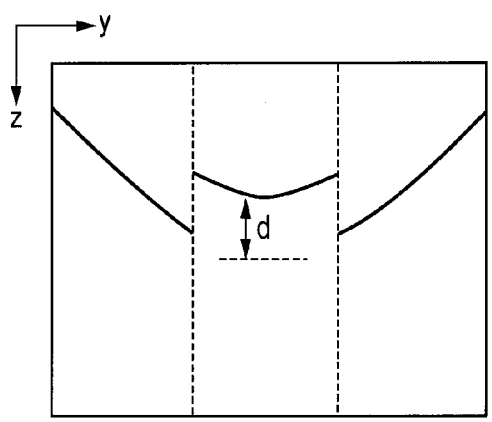

In Step S1001, in order to photograph the object to be inspected, positions in the plane direction and in the depth direction are adjusted. Here, with reference to FIGS. 11A to 11C, there is described a case where the object to be inspected is the model eye. In addition, it is supposed that the coherence gate position is set to the upper part of the image. FIG. 11A illustrates the YZ plane of the tomographic image obtained by photographing the model eye. Here, a position in the depth direction is adjusted so that the model eye is clearly photographed. FIG. 11B illustrates the YZ plane of the tomographic image in the case where the three coherence gate positions are operated in conjunction with one another. Further, FIG. 11C illustrates the YZ plane of the tomographic image in the case where only the center coherence gate position is moved. As illustrated in FIG. 11B, when the three coherence gate positions are operated in conjunction with one another, the retina layer moves up and down while maintaining its shape. However, as illustrated in FIG. 11C, in the case where the coherence gate positions are moved independently, the shape of the retina layer cannot be maintained. Therefore, a movement amount d for moving the coherence gates independently as illustrated in FIG. 11C is stored in the memory unit 912.

(Step S1004)

In Step S1004, an image processing unit 913 performs the volume image deformation correction using the shape model in consideration of the movement amount d of the coherence gate. This process is described with reference to FIG. 10B.

(Step S1011)

In Step S1011, the correction unit 934 performs the position correction of the tomographic image in the depth direction using the movement amount d of the coherence gate positions that are moved independently. When initial setting of the apparatus is performed, correspondence between the movement amount of the coherence gate and pixels in the tomographic image is checked for each measuring light beam. The correspondence between the movement amount of the coherence gate and image pixels in this embodiment is shown in Table 1. In Table 1, a feed pitch of the coherence gate in this embodiment is 2000.

TABLE 1

|  | Measuring light 1 | Measuring light 2 | Measuring light 3 |
|---|---|---|---|
| Gate position difference (with reference to measuring light beam 2) | −3.5 mm (−5800) | 0 | −1.8 mm (−3000) |
| Image pixel and gate feed pitch | 170 pixel/ 2000 | 176 pixel/ 2000 | 172 pixel/ 2000 |
| Gate feed pitch distance | ~1.19 mm/ 2000 | ~1.22 mm/ 2000 | ~1.20 mm/ 2000 |

As illustrated in Table 1, if the correspondence between the movement amount of the coherence gate and image pixels is checked in advance for each measuring light beam, the movement amount of pixels in the tomographic image can be calculated from the movement amount d for independently moving the coherence gates. For instance, moving the position of only the center coherence gate (measuring light 2 in Table 1) by 500 is the same as moving the tomographic image by 44 pixels. Therefore, the correction unit 934 determines the movement amount in the tomographic image from the movement amount d for moving the coherence gates independently for each measuring light beam, and corrects the retina layer depth position of the tomographic image. Note that, the numeric values in Table 1 are example values in this embodiment and should not be interpreted as a limitation.

In this embodiment, there is described an example in which the coherence gates are moved independently in photographing, but this should not be interpreted as a limitation. For instance, it is possible to shift the coherence gate positions when the initial setting of the apparatus is performed. By setting the position of the object to be photographed closer to the coherence gate for photographing, there is higher probability that a clearer image can be obtained. The retina layer usually has a curved shape, and hence the center coherence gate position may be set to be shifted from the beginning, and all the coherence gates may be operated in conjunction with one another in photographing. If the shift is set at the initial setting, the shift amount of the coherence gate position from the position where the shape of the object to be inspected is restored is stored in the memory unit 912, and the shift amount is corrected so as to estimate the shape model.

According to the structure described above, coherence gate positions of the measuring light beams are changed independently when the volume image is photographed with a plurality of measuring light beams. Then, the retina layer is detected from a plurality of tomographic images obtained by photographing spatially separated points at the same time, and the shape model is estimated by correction based on the change quantity for independently changing positions of the detected retina layer. Then, by correcting the volume image deformation using the shape model, the volume image deformation can be corrected accurately also in the volume image in the case where the coherence gate positions are independently moved.

Other Embodiments

The present invention is realized also by performing the following process. Specifically, software (program) for realizing the functions of the embodiments described above is supplied to a system or an apparatus via a network or a various types of storage media, and a computer (or CPU or MPU) of the system or the apparatus reads out the program so as to execute the program.

The present invention is not limited to the embodiments described above, which can be modified or changed variously within the scope of the present invention without deviating from the spirit thereof. For instance, the above-mentioned embodiments describe the case where the object to be measured is an eye, but the present invention can be applied to an object to be measured such as skin or organs other than the eye. In this case, the present invention includes an exemplary embodiment as medical equipment such as an endoscope other than an ophthalmological apparatus. Therefore, it is desired that the present invention be understood as an inspection apparatus such as an ophthalmological apparatus, and that the eye to be inspected be understood as an exemplary embodiment of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-105391, filed May 10, 2011, which is hereby incorporated by reference herein in its entirety.

What is claimed is:

1. An image processing apparatus, comprising:
   an image acquiring unit configured to acquire a three-dimensional image of a fundus of an eye to be inspected based on a plurality of combined light beams obtained by combining a plurality of return light beams from the eye to be inspected that is irradiated with a plurality of measuring light beams simultaneously, and a plurality of reference light beams respectively corresponding to the plurality of return light beams;
   a detection unit configured to detect a normal retina layer from each of a plurality of tomographic images obtained by photographing the fundus at a predetermined timing among a plurality of tomographic images constituting the three-dimensional image;
   an estimation unit configured to estimate a fundus shape based on the detected normal retina layer; and
   a correction unit configured to correct a positional deviation between the plurality of tomographic images constituting the three-dimensional image based on the estimated fundus shape.

2. An image processing apparatus according to claim 1, wherein the estimation unit estimates the fundus shape based on the detected normal retina layer in a plurality of tomographic images photographed at the same time among the plurality of photographed tomographic images.

3. An image processing apparatus according to claim 2, wherein the estimation unit divides the plurality of photographed tomographic images into a plurality of sets each of which includes a plurality of tomographic images photographed at the same time, and estimates the fundus shape for each set.

4. An image processing apparatus according to claim 1, wherein the detection unit judges a normal layer structure part and an abnormal layer structure part, and the estimation unit estimates the fundus shape from the normal layer structure part detected by the detection unit.

5. An image processing apparatus according to claim 1, further comprising a control unit configured to control a value of each of interference distances of the plurality of measuring light beams, wherein the correction unit corrects a retina layer position of the each of the plurality of tomographic images based on the controlled value.

6. An image processing apparatus according to claim 1, further comprising a scanning unit configured to scan the plurality of measuring light beams in a main scanning direction and in a sub scanning direction,
wherein the estimation unit estimates the fundus shape in the sub scanning direction.

7. An image processing apparatus according to claim 6, wherein the plurality of measuring light beams irradiate positions separated by a predetermined interval in the sub scanning direction.

8. An image processing method, comprising:
acquiring a three-dimensional image of a fundus of an eye to be inspected based on a plurality of combined light beams obtained by combining a plurality of return light beams from the eye to be inspected that is irradiated with a plurality of measuring light beams simultaneously, and a plurality of reference light beams respectively corresponding to the plurality of return light beams;
detecting a normal retina layer from each of a plurality of tomographic images obtained by photographing the fundus at a predetermined timing among a plurality of tomographic images constituting the three-dimensional image;
estimating a fundus shape based on the detected normal retina layer; and
correcting a positional deviation between the plurality of tomographic images constituting the three-dimensional image based on the estimated fundus shape.

9. A non-transitory storage medium having stored therein a program for causing a computer to execute the steps of the image processing method according to claim 8.

10. An image processing apparatus, comprising:
an image acquiring unit configured to acquire a three-dimensional image of a fundus of an eye to be inspected based on a plurality of combined light beams obtained by combining a plurality of return light beams from the eye to be inspected that is irradiated with a plurality of measuring light beams, and a plurality of reference light beams respectively corresponding to the plurality of return light beams;
a detection unit configured to detect a retina layer from each of a plurality of tomographic images obtained by photographing the fundus at the same time among a plurality of tomographic images constituting the three-dimensional image;
an estimation unit configured to estimate a fundus shape based on the detected retina layer; and
a correction unit configured to correct a positional deviation between the plurality of tomographic images constituting the three-dimensional image based on the estimated fundus shape.

11. An image processing method, comprising:
acquiring a three-dimensional image of a fundus of an eye to be inspected based on a plurality of combined light beams obtained by combining a plurality of return light beams from the eye to be inspected that is irradiated with a plurality of measuring light beams, and a plurality of reference light beams respectively corresponding to the plurality of return light beams;
detecting a retina layer from each of a plurality of tomographic images obtained by photographing the fundus at the same time among a plurality of tomographic images constituting the three-dimensional image;
estimating a fundus shape based on the detected retina layer; and
correcting a positional deviation between the plurality of tomographic images constituting the three-dimensional image based on the estimated fundus shape.

12. A non-transitory storage medium having stored therein a program for causing a computer to execute the steps of the image processing method according to claim 11.

13. An image processing apparatus, comprising:
an image acquiring unit configured to acquire a three-dimensional image of a fundus of an eye to be inspected based on a plurality of combined light beams obtained by combining a plurality of return light beams from the eye to be inspected that is irradiated with a plurality of measuring light beams, and a plurality of reference light beams respectively corresponding to the plurality of return light beams;
a detection unit configured to detect a normal retina layer from each of a plurality of tomographic images obtained by photographing the fundus at a predetermined timing among a plurality of tomographic images constituting the three-dimensional image;
an estimation unit configured to estimate a fundus shape based on the detected normal retina layer; and
a correction unit configured to correct a positional deviation between the plurality of tomographic images constituting the three-dimensional image based on the estimated fundus shape.

14. An image processing method, comprising:
acquiring a three-dimensional image of a fundus of an eye to be inspected based on a plurality of combined light beams obtained by combining a plurality of return light beams from the eye to be inspected that is irradiated with a plurality of measuring light beams, and a plurality of reference light beams respectively corresponding to the plurality of return light beams;
detecting a normal retina layer from each of a plurality of tomographic images obtained by photographing the fundus at a predetermined timing among a plurality of tomographic images constituting the three-dimensional image;
estimating a fundus shape based on the detected normal retina layer; and
correcting a positional deviation between the plurality of tomographic images constituting the three-dimensional image based on the estimated fundus shape.

15. A non-transitory storage medium having stored therein a program for causing a computer to execute the steps of the image processing method according to claim 14.

16. An image processing apparatus according to claim 5, wherein the control unit controls the value of each interference distances by changing an optical path length of each of the plurality of the reference lights to move each of positions of retina layers corresponding to each of the plurality of the reference lights, so as to eliminate deviations between the positions of retina layers in tomographic image.

17. An image processing method according to claim 8, wherein the fundus shape is estimated based on the retina layer in a plurality of tomographic images photographed at the same time among the plurality of photographed tomographic images.

18. An image processing method according to claim 8, wherein the detected retina layers are judged as a normal layer structure part or an abnormal layer structure part, and the fundus shape is estimated from the normal layer structure part detected by the detection unit.

19. An image processing method according to claim 8, further comprising a step of controlling a value of each of interference distances of the plurality of measuring light beams, wherein a retina layer position of the each of the plurality of tomographic images is corrected based on the controlled value.

* * * * *